United States Patent [19]

Chaussee

[11] Patent Number: 4,970,220

[45] Date of Patent: Nov. 13, 1990

[54] SKIN CONDITIONING COMPOSITION

[75] Inventor: James G. Chaussee, Racine County, Wis.

[73] Assignee: S. C. Johnson & Son, Inc., Racine, Wis.

[21] Appl. No.: 273,135

[22] Filed: Nov. 14, 1988

Related U.S. Application Data

[60] Continuation of Ser. No. 844,411, Mar. 26, 1986, abandoned, which is a continuation of Ser. No. 646,880, Sep. 4, 1984, abandoned, which is a division of Ser. No. 378,695, May 17, 1982, Pat. No. 4,978,853.

[51] Int. Cl.$^5$ .............................................. A61K 31/44
[52] U.S. Cl. ..................................... 514/358; 424/59; 424/63; 424/65; 424/70; 424/73; 514/844; 514/845; 514/846; 514/847
[58] Field of Search ........................ 424/59, 63, 65, 70, 424/73; 514/358, 844, 845, 846, 847

[56] References Cited

U.S. PATENT DOCUMENTS

| | | | |
|---|---|---|---|
| 4,014,995 | 3/1977 | Juliano et al. | 514/783 |
| 4,055,634 | 10/1977 | Brenner et al. | 424/47 |
| 4,070,450 | 1/1978 | Barner et al. | 424/59 |
| 4,272,544 | 6/1981 | Cella et al. | 424/365 X |
| 4,374,125 | 2/1983 | Newell | 424/70 |
| 4,556,557 | 12/1985 | Reichert | 424/94.6 |
| 4,668,513 | 5/1987 | Reichert | 422/94 |

FOREIGN PATENT DOCUMENTS

| | | |
|---|---|---|
| 955093 | 12/1956 | Fed. Rep. of Germany . |
| 966040 | 6/1957 | Fed. Rep. of Germany . |
| 1492125 | 9/1969 | Fed. Rep. of Germany . |
| 1042499 | 9/1966 | United Kingdom . |
| 1283892 | 8/1972 | United Kingdom . |
| 2008943 | 6/1979 | United Kingdom . |

OTHER PUBLICATIONS

USAN and the USP Dictionary of Drug Names, USAN 1980 (1961–1979 cumulative list), pp. 11, 39, 44 and 343.
Olympus Cocoa Butter U.S.P./N.F., R. W. Greef & Co., Inc., Greenwich, Conn., one page, undated.
Chemical Abstracts 97:98382b.
Chemical Abstracts 53:15498c.
Jellinek, Formulation and Function of Cosmetics, Wiley-Interscience, 1970, pp. 141–152, 161–166, 351–364, 372–376, 393–394, 402, 406.
Windholz, ed., The Merck Index, Merck & Co., Inc., 1976, p. 909.
Hawley, The Condensed Chemical Dictionary, Tenth Edition, pp. 502–503, 537, 960 (1981).

Primary Examiner—John W. Rollins

[57] ABSTRACT

An on-occlusive base composition for personal care compositions providing enhanced conditioning and protection against dryness includes a panthenyl moisturizer and an emollient which includes a polyhydric alcoholic humectant and a polyether derivative.

20 Claims, No Drawings

SKIN CONDITIONING COMPOSITION

This is a continuation of U.S. Ser. No. 06/844,411, filed on Mar. 26, 1986 and now abandoned, which is a continuation of U.S. Ser. No. 06/646,880, filed on Sept. 4, 1984 and now abandoned, which was a division of U.S. Ser. No. 06/378,695, filed on May 17, 1982 and now U.S. Pat. No. 4,478,853.

BACKGROUND OF THE INVENTION

1. Field of The Invention

The present invention relates to an improved, topically applied base composition providing enhanced conditioning for personal care compositions. In particular, it relates to a non-occlusive moisturizing base for imparting extended skin care properties to conditioning gels, lotions, cremes, sticks, splashes and sprays.

2. Description of The Prior Art

It has long been desired to provide body conditioning and refreshment without the heavy, greasy and occlusive characteristics of vaseline-mineral oil- and lanolin-based compositions. Skin and scalp conditioning is recognized as a necessary adjunct to reduce or prevent harmful drying effects to the skin and hair caused by use of detergents, toilet bar soaps, shampoos, antiperspirants and the like. It is also well understood that the drying and cracking effects on the skin caused by extended exposure to the sun and low humidity requires an effective conditioner and moisturizer to return cutaneous tissue to its normal softness and moisture levels.

It is now understood that from a biochemical standpoint, dryness is, in part, a measure of the water content of the skin. The skin becomes dry because of excessive loss of water from its surface and the subsequent loss of water from the stratum corneum. Continuous and prolonged immersion in various soaps and detergents, use of shampoos and antiperspirants and exposure to the sun or infrared and/or ultraviolet radiation all contribute to drying the stratum corneum. Surfactant based cleansers including soaps and shampoos promote dissolution of skin surface lipids, horny layer lipids and hydroscopic water-soluble components in the corneum. This, in turn, leads to the development of so called "dry skin" with concomitant cracking, flaking and scaling of dead corneocytes.

It has long been a desideratum of the personal care industry to find a non-oily, water-soluble base composition which would permit satisfactory removal of excess surface oil, soil and skin debris, but would allow recovery of normal oil levels, thus protecting the skin surface from drying out and from losing needed moisture to permit it to maintain an attractive appearance. Such a vehicle or base, when employed in the full spectrum of skin and hair care products, would assist in maintaining oil content, reducing scaling and increasing removal of preexisting scale. When employed in after-bath and shower body splashes, it would refresh and condition the skin while providing extended protection against drying out.

Various synthetic and natural emollients have been proposed to allow recovery of normal oil levels, when used in combination with or after use of, detergents, soaps or other surfactants. However, none have been entirely satisfactory.

Measurement of "conditioning" effects has proven elusive and uncertain as illustrated in Pavlichko, et al., *COSMETIC TECHNOLOGY*, pp. 40–42, June 1981. One accepted measure of emolliency is made with a sebumeter which quantifies levels of surface oil on the skin. Another useful measurement of emollience is made by tape-stripping treated skin to remove dead corneocytes from its surface to indicate the degree of dryness of the skin. Slides of treated skin taken with a scanning electron microscope illustrate whether or not a protective film is formed over the skin and the nature of such a film.

Typical cosmetic formulations to help prevent formation of dry, scaling skin are disclosed in U.S. Pat. Nos. 4,268,502, 4,268,526 and 4,272,544. These patents disclose cleansers, tonics, cremes and lotions containing certain of the key ingredients of the present invention, but not the vehicle or base composition which is an important part of the present invention.

SUMMARY OF THE INVENTION

It is, therefore, an object of the present invention to provide a water-soluble base composition compatible with personal care, various topical drugs and insect repellent compositions which is non-oily and non-occlusive yet which imparts enhanced emolliency or moisturizing properties and provides extended protection against formation of dry, scaling skin.

It is another object of the invention to provide an after bath and shower body splash which refreshes and conditions the skin and imparts prolonged protection against drying of cutaneous tissue.

It is an additional object to provide cosmetic skin and treating compositions which cleanse, soften and condition while inhibiting scaling, flaking, drying out and other causes of skin irritation.

These and other objects are attained in a non-oily, non-occlusive, water-soluble base composition for personal care compositions providing enhanced skin or hair conditioning and extended protection against drying comprising (a) a panthenyl moisturizer and (b) an emollient comprising a polydric alcoholic humectant and a polyether derivative, wherein the weight ratio of the moisturizer (a) to the emollient, (b) is sufficient to provide effective conditioning and maintain cutaneous moisture and oils levels.

As employed herein the phrase "panthenyl moisturizer" refers to DL-panthenol and its derivatives.

The interaction between the panthenyl moisturizer and the emollient in the base composition imparts significant beneficial cosmetic properties to the skin, hair and scalp. High levels of emolliency are provided, while flaking, scaling and redness are reduced for extended periods. The skin remains soft, supple and smooth for hours after such treatment, while moisture and oils levels necessary to reduce or prevent dryness, flaking and scaling, are maintained.

Enhanced results are obtained when the base composition is a blend of (a) DL-panthenol, (b) a polyhydric alcohol, preferably glycerol, and (c) a polyether derivative, preferably a copolymer of polyethylene glycol and polypropylene glycol. The blend is topically applied in any appropriate form, as a cream, gel, lotion, stick, hydroalcoholic or aqueous solution, emulsion or spray. The polyhydric alcoholic humectant and polyether derivative are each preferably employed in the base composition in a weight ratio to panthenyl moisturizer from about 0.28:1 to about 15:1.

When the base composition is employed as an aqueous conditioning composition containing other ingredients such as other emollients, gelling agents, neutralizing agents, lubricants, cleansers, emulsifiers and medicaments and the like, from about 1 to 4.2 weight percent of said polyhydric alcoholic humectant is employed; from about 1 to 4.2 weight percent of said polyether derivative is employed and from about 0.3 to 3.6 weight percent of said panthenyl moisturizer is employed, based on the total weight of the composition. Unless otherwise noted all weights are based on the total weight of the composition.

DESCRIPTION OF PREFERRED EMBODIMENTS

The panthenyl moisturizer of the present invention provides increased emolliency, reduces the tendency of skin to scale, redden and flake and promotes removal of scaly layers without occluding the skin pores or forming the oily, greasy film which characterizes petroleum jelly, mineral oil or lanolin formulations. Typical moisturizers include, dexpanthenol, calcium pantothenate, Royal Jelly, panthethine, pantetheine, panthenyl ethyl ether, pangamic acid, pyridoxin (vitamin $B_6$), pantoyl lactone, vitamin B complex and other DL-panthenol derivatives. Enhanced results are obtained and accordingly, it is preferred to utilize DL-panthenol as the moisturizer.

The emollient of the invention includes a polyhydric alcoholic humectant and a polyether derivative. The humectant aids in increasing emollience, reducing scaling, stimulating removal of built-up scale and improving the clarity of the film formed on skin on or after application. Typical polyhydric alcohols employed in the invention include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerol.

The polyether derivative acts to reduce scaling, increases emollience and improves the clarity of the base composition, on application. For this and other purposes useful polyether derivatives include poly (ethylene oxide) homopolymers, (molecular weight 100,000–5,000,000), poly (propylene oxide) homopolymers, polyoxypropylene derivatives of trimethylolpropane and other suitable poly (alkylene oxide) homo- and copolymers. Preferred polyether derivatives are the copolymers of polyethylene glycol and polypropylene glycol having a molecular weight from about 1000 to 2000, including polyoxyethylene/polyoxypropylene glycols. The most preferred polyether derivative is a polyethylene glycol/polypropylene glycol copolymer having a molecular weight of about 1300, formed from copolymerizing 17 moles of polyethylene glycol per 6 moles of polypropylene glycol.

The amount of water or aqueous carrier to be included in the skin care compositions employing the base composition of the invention will vary, depending upon the desired consistency of the final product. By varying the amount of water, gelling agent and/or surfactant present, it is possible to formulate a thick-flowing liquid or lotion, a semi-liquid thick cream, a paste, a stick, a gel, an alcoholic hydrogel, an emulsion, an alcoholic solution or a formulation suitable for use in an aerosol. In any event, the cosmetic composition should be provided in a form which can be uniformly spread on the skin. For this and other purposes, deionized water is preferred as the aqueous carrier.

The base composition of the invention which can be formulated into a desired personal care product contains an effective amount of panthenyl moisturizer, polyhydric alcoholic humectant and polyether derivative to enhance emollience, reduce scaling and drying and to provide a clear film on application. For this and other purposes the weight ratio of emollient to moisturizer in the base composition is from about 33:1 to 0.54:1 and preferably from about 18:1 to 3:1. The weight ratio of humectant to moisturizer is generally from about 15:1 to 0.28:1, preferably from about 10:1 to 3.2:1. The weight ratio of polyether derivative to moisturizer is usually from about 15:1 to 0.28:1, and preferably from about 10:1 to 1.2:1.

When employed in an aqueous skin care product the proportions of ingredients are generally as follows:

| Ingredient | Weight Percent Of Total Composition |
|---|---|
| panthenyl moisturizer | up to 5% |
| polyhydric alcoholic humectant | up to 5% |
| polyether derivative | up to 5% |

Enhanced results are obtained and accordingly, it is preferred to employ from about 0.3 to 3.6 percent by weight moisturizer, and preferably from about 0.4 to 1.1 percent by weight; from about 1 to 4.2 percent by weight of humectant and preferably from about 2.5 to 3.6 percent by weight; and from about 1 to 4.2 percent by weight of polyether derivative and preferably, from about 1.4 to 3.6 percent by weight, in a skin care composition.

The base composition may be formulated into an aqueous solution for skin care applications, preferably a hydroalcoholic solution or gel. In alcohol-containing formulations the alcohol employed is a non-toxic, lower alkanol, including n-propanol, isopropanol or more preferably, ethanol. The alcohol may be employed with any conventional denaturing compound compatible with cosmetics. The alcohol is usually present in amounts to about 55% by weight to provide satisfactory stability, and is preferably employed in amounts from about 35 to 50% by weight.

In order to improve the lubricity of these and other personal care compositions and to provide emollience without a greasy feel, a silicone oil or fluid is preferably employed, such as a dimethyl polysiloxane, a methylphenyl polysiloxane and water-soluble, and an alcohol-soluble silicone glycol copolymer. Preferred siloxanes include dimethyl polysiloxane (CTFA name—dimethicone)—a polysiloxane end-blocked with trimethyl units and polydimethylcyclosiloxane, (CTFA name—cyclomethicone). The preferred siloxanes exhibit a viscosity from about 2 to 50 centistokes at 25° C. The siloxanes are employed in sufficient amounts to aid in stimulating removal of scale and to aid in controlling conditioning, usually from about 0 to 10% by total weight of composition, preferably from about 1 to 3%.

The personal care compositions of the invention may also include a thickener or gelling agent to provide viscosity control, to stabilize the composition and to increase emolliency. A variety of gelling agents may be employed. The preferred gelling agents are interpolymers of a monomeric monoolefinic acrylic acid being crosslinked with from 0.1 to 10% by weight of a monomeric polyether of an oligosaccharide in which the hydroxyl groups are etherified with alkyl groups at the rate of at least two alkyl ether groups per oligosaccharide molecule. Essentially, these gelling agents are colloidal water-dispersible acrylic acid polymers crosslinked with from 0.75 to 2% of a crosslinker, such as polyallylsucrose or polyallyl pentaerythritol.

Commercially available interpolymeric gelling agents are marketed by B. F. Goodrich Chemical Co. under the tradename Carbopol, having molecular weights of about one million. The various Carbopols also designated "carbomers" are distinguished from each other on the basis of viscosity. The preferred polymers include Carbopol 934 Brookfield viscosity 30,000–40,000 and Carbopol 941 Brookfield viscosity 4000–11,000 and most preferably, Carbopol 940 Brookfield viscosity 40,000–60,000. The polymers are gelled by partially or completely neutralizing them with an alkaline material such as triethanolamine, triethyl amine, isopropyl amine, potassium hydroxide, sodium hydroxide, and the like. Other gelling agents or thickeners which can be employed include hydroxypropyl cellulose polymers, disclosed in U.S. Pat. No. 3,485,915, natural and synthetic gums and the like.

In general, the amounts of gelling agent employed will depend upon the particular formulation to be prepared. Usually up to about 50% by weight will be sufficient. For hydroalcoholic solutions, from about 0.1 to 1 weight percent and preferably from 0.2 to 0.8 weight percent is employed, together with from about 0.05 to 0.5 and preferably 0.1 to 0.4 weight percent of a neutralizing agent. Deionized water is added as required.

In general the base composition is employed in formulations in suitable amounts to provide effective conditioning and dry skin control. Usually from about 1 to 15 percent by weight of the total weight of the composition is an effective amount of base composition, although greater or lesser amounts can also be employed.

The base composition of the invention can also be prepared in an aqueous lotion from. Preferably from 1 to 10 weight percent of an emulsifier of the nonionic, anionic, amphoteric or cationic class, is employed in the lotion to stablize it.

Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglyceride wherein the fatty acid moiety contains from 10 to 20 carbon atoms, diethylene glycol, polyethylene glycols of molecular weight 200 to 6000, propylene glycol of molecular weight 200 to 3000, sorbitol, sorbitan, polyoxyethylene sorbitol, polyoxyethylene sorbitan, and hydrophilic wax esters.

Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units.

Satisfactory cationic emulsifiers are the quaternary ammonium, morpholinium and pyridinium compounds.

Satisfactory amphoteric emulsifiers are cocobetaines, lauryl dimethylamine oxide and cocoylimidazoline.

Other emollients can be employed, if desired, in the skin and hair care compositions of the invention. Those emollients, include the following classes:

1. Hydrocarbon oils and waxes. Examples thereof are mineral oil, petrolatum, paraffin, ceresin, ozokerite, microcrystalline wax, polyethylene, and perhydrosqualene.

2. Triglyceride esters, for example vegetable and animal fats and oils. Examples include castor oil, cocoa butter, safflower oil, cottonseed oil, corn oil, olive oil, cod liver oil, almond oil, avocado oil, palm oil, sesame oil, squalane, and soybean oil.

3. Acetoglyceride esters, such as acetylated monoglycerides.

4. Ethoxylated glycerides, such as ethoxylated glyceryl monostearate.

5. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

6. Alkenyl esters of fatty acids having 10 to 20 carbon atoms. Examples thereof include oleyl myristate, oleyl stearate, and oleyl oleate.

7. Fatty acids having 10 to 20 carbon atoms. Suitable examples include pelargonic, lauric, myristic, palmitic, stearic, isosteaaric, hydroxystearic, oleic, linoleic, ricinoleic, arachidic, behenic, and erucic acids.

8. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanol alcohols are examples of satisfactory fatty alcohols.

9. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups.

10. Ether-esters such as fatty acid esters of ethoxylated fatty alcohols.

11. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

12. Polyhydric alcohol esters. Ethylene glycol mono- and di-fatty acid esters, diethylene glycol mono-and di-fatty acid esters, polyethylene glycol (200–6000) mono- and di-fatty acid esters, propylene glycol mono- and di-fatty acid esters, polypropylene glycol 2000 mono-oleate, polypropylene glycol 2000 monostearate, ethoxylated propylene glycol monostearate, glyceryl mono- and di-fatty acid esters, polyglycerol poly-fatty esters, ethoxylated glyceryl monostearate, 1, 3-butylene glycol monostearate, 1, 3-butylene glycol distearate, polyoxyethylene polyol fatty acid ester, sorbitan fatty acid esters, and polyoxyethylene sorbitan fatty acid esters are satisfactory polyhydric alcohol esters.

13. Wax esters such as beeswax, spermaceti, myristyl myristate, stearyl stearate.

14. Beeswax derivatives, e.g. polyoxyethylene sorbitol beeswax. These are reaction products of beeswax with ethoxylated sorbitol of varying ethylene oxide content, forming a mixture of ether-esters.

15. Vegetable waxes including carnauba and candelilla waxes.

16. Phospholipids such as lecithin and derivatives.

17. Sterols. Cholesterol, cholesterol fatty acid esters are examples thereof.

18. Amides such as fatty acid amides, ethoxylated fatty acid amides, solid fatty acid alkanolamides.

Emollients which may be included in a typical lotion formulation include, for example, a vegetable or mineral oil, a fatty acid ester, and/or a fatty alcohol. These are incorporated in amounts up to about 30% by weight of the total composition. Deionized water is added, as required.

If desired, the base composition of the invention is formulated into a skin cream. In this form, other suitable emollients are also employed therein, such as a fatty acid, lanolin, a fatty alcohol ether and an alcohol ester in amounts up to about 30% of the total weight of the aqueous composition. A suitable emulsifier may also be employed in amounts from about 3 to 20% by weight. An aqueous carrier, preferably deionized water is added as required.

The base composition can also be formulated into a desired personal care product and packaged under pressure in an aerosol container together with a gaseous propellant, such as (i) a fluorinated hydrocarbon, especially Freon, (ii) nitrogen or, more preferably, (iii) a volatile hydrocarbon, as butane, propane, isobutane or mixtures thereof.

The base composition may also be formed into an aqueous or hydroalcoholic gel. The hydroalcolic gel contains a lower alkanol and neutralized thickener as required to provide an appropriately viscous formulation. Generally from about 40 to 55% alcohol and from about 0.1 to 1% thickener is employed. If desired, in the aqueous gel, a surfactant can be employed in amounts from about 1 to 10 weight percent to provide adequate dispersion and stabilization.

The base composition may also be utilized in the form of a milky or creamy oil-in-water emulsion employing a fatty acid, alcohol or oil, stabilized by a surfactant and a neutralized thickening agent.

The base compositions of the invention are also formulated into solid forms, such as a stick, for use as a deodorant, lip balm, sunscreen or the like. For this purpose thickeners, such as crosslinked acrylic acid interpolymers (carbomers), polyethylene glycols, gums, methylcellulose and bentonite and emulsifiers, such as fatty acid soaps, may be employed. The total amount of thickener for the solid formulations is from about 1 to 20%, preferably 5 to 15% by weight. From about 1 to 10%, preferably 2 to 5% by weight of emulsifier is utilized.

Other conventional additives typically employed in cosmetic compositions may be employed. Fragrance oils, which mask the odor of the base and provide cosmetic appeal, can be employed, usually in amounts from 0.005% to 2%. Nontoxic and compatible dyes may be utilized to color the composition, as desired. Preservatives, such as methylparaben or other esters of parahydroxy benzoic acid, can be employed, generally in amounts from about 0.01% to 0.2%. If desired, formaldehyde and other similar preservatives can also be utilized.

In addition, other ingredients can be employed beneficially to provide a specifically tailored cosmetic composition. For example, a sun screen additive, such as salicylic acid derivatives, cinnamic acid derivatives, benzophenone derivatives, coumarin derivatives, azoles, imidazole derivatives, naphtosulfonates, quinine salts and hydroquinone and its derivatives, especially benzylidene camphor, ethylhexyl para methoxy cinnamate, 5-benzoyl-4-hydroxy methoxy benzene sulfonic acid and octyl dimethyl para-aminobenzoic acid can be employed in the inventive composition in amounts from about 1% to 8% by weight of the total composition.

To provide a skin protectant composition, zinc oxide and like ingredients can be provided in amounts from about 0.5% to 3% by weight of the composition.

Essential oils, such as menthol, quaternary ammonium salts, soap solutions and the like can also be employed to provide formulations providing specific beneficial treatment. Additional active materials that can be incorporated to provide certain benefits such as insect repellend materials such as N,N-diethyl-m-toluamide, 2-ethyl-1,3-hexanediol, various active drug ingredients including pharmaceuticals and over-the-counter drug active ingredients: antipruritics such as hydrocortisone, hydrocortisone acetate and the like; topical anesthetics such as benzocaine, lidocaine, dibucaine, pramoxine, hydrochloride and the like; topical analgesics such as methyl salicylate, camphor, menthol resorcinol and the like; skin wound protectants such as hexylresorcinol, phenol, tetracycline hydrochloride and the like; topical antiseptics such as benzalkonium chloride, povidone-iodine and the like; anti-acne aids such as benzoyl peroxide and the like.

The base composition of the invention can be formulated into face creams, hand and body lotions, after shave lotions, shave creams, sunscreen creams, lotions and gels, colognes, perfumes, shampoos, creme rinses, hydroalcoholic refresher-conditioner gels, aerosol sprays, liquid skin and scalp cleansers, stick deodorants and/or antiperspirants and the other myriad spectrum of personal care products. In general the total amount of the base composition in these compositions can vary from about 1 to 100% and is preferably from about 1 to 20% by weight of the composition.

The base composition of the invention may be prepared by simply mixing the panthenyl moisturizing agent and the emollient blend in accordance with conventional procedures.

A preferred hydroalcoholic gel is prepared by charging a lower alkanol, as denatured ethanol and a silicone oil, as dimethyl polysiloxane, to a mixing pot with agitation. To the resulting blend is sifted the gelling agent such as Carbopol 940, until it is completely dispersed and wetted. Cocoa butter, a natural skin softener, is melted, by heating to about 100° F. and is added to the mixture. To this blend is added a preferred base composition; glycerol, polyethylene glycol/polypropylene glycol copolymer, DL-panthenol and also a fragrance, a coloring agent and water. The resulting mix is stirred until it is thoroughly dispersed and uniform. A gelling agent neutralizer, triethanolamine, is added with continued mixing until the resulting blend is thick and uniform to provide a conditioning, refreshing afterbath and shower gel product.

The cosmetic compositions of the invention may be prepared by a batch operation or by in-line blending techniques. In preparing a hydroalcoholic conditioning skin refresher by a batch operation, the water, gelling agent, emollients, moisturizer, dyes and fragrances are added, mixed to uniformity at appropriate temperatures from 70°–120° F. depending on melting points of ingredients and thereafter the lower alkanol is blended in. After the mix becomes uniform, the gelling agent is neutralized to achieve the ultimate desired viscosity.

In the in-line blending process, a batch of concentrated ingredients is made as in the batching process prior to addition of the alkanol. The concentrate is then blended in-line through static mixers with an alkanol. Finally, the neutralizing agent is metered in and the finished product is pumped through a series of static and/or dynamic mixers to achieve uniformity and proper viscosity.

The skin care compositions of the present invention are topically applied in a conventional manner, as by dispersing from a container, an aerosol spray can or a pump spray. The compositions are rapidly absorbed and leave the skin with a soft and smooth appearance.

The alcoholic compositions provide immediate refreshment to the skin and leave it feeling non-oily, supple, smooth and moisturized.

The viscosity of the various personal care compositions may vary widely. However, for easy dispersing and enhanced stability it is generally preferred to employ compositions at viscosities from 2000 to 20,000 cps. At less than 2000 cps the compositions exhibit reduced stability; while above about 20,000 cps, dispersing becomes difficult.

The base composition of the invention, a panthenyl moisturizer and an emollient blend of polyhydric alcoholic humectant and polyether derivatives and the representative personal care compositions made therefrom were demonstrated to exhibit enhanced conditioning, clear film formation, and dry skin reduction with reduced scale, primarily through objective testing with a sebumeter, a gloss meter and utilizing tape stripping and also through subjective consumer tests.

In the sebumeter tests, subjects had about 0.5 gram of product applied to an area of skin 5 cm by 20 cm with rubbing until uniform application was achieved. Prior to this application a baseline reading was obtained of the test site. After application, readings were taken at 5, 10, 15 and 30 minutes. Sebumeter testing is an indication of the oil content at the skin surface. The higher the reading the greater the moisturizing.

The tape stripping test removes dead corneocytes (scale) from the surface of the skin and is an indication of the degree of dryness of the skin. To develop a baseline, a piece of clear cellophane tape ¼ inch by 1-½ inches is applied to the test site using firm pressure control. The tape is removed as a control. Then, to a clean forearm is applied about 0.5 gram of product to an area 5 cm by 20 cm. The product is uniformly applied. Clear cellophane tape is applied to the test site and removed from the test site at 15, 30, 60, 90 and 120 minutes after application. Half the tape is placed on the treated area and the other half on the untreated control area adjacent the treated site. The more dead white skin removed, the whiter the tape. The lower the test values the higher the oils and water content of the skin.

Stereophotomicrographs were taken on untreated forearms and after using a conditioning skin refresher of the invention. These photomicrographs showed a protective non-occlusive film was formed with the inventive formulations for up to four hours.

The skin care products of the invention have been shown to have no effect on transepidermal water loss (TEWL). TEWL is a measure of the occlusive effect of a formulation. The lack of change in TEWL values as compared to an untreated control area confirms the non-occlusive nature of the film produced by the present invention. In general, it was believed that to obtain satisfactory conditioning and softening, an occlusive film was necessary to prevent water and oil loss from the skin. The present invention does not require a greasy, oily occlusive film, which blocks pores and can cause discomfort.

The following Examples serve to illustrate certain preferred embodiments of the invention and are not illustrative of scope.

EXAMPLE I

A skin care composition of the invention was prepared as follows:

Into a mixing pot is charged denatured alcohol (SDA 40 alcohol); dimethicone (Dow Corning 225 Fluid)—dimethylpolysiloxane and cyclomethicone (Dow Corning 344 Fluid)—polydimethylcyclosiloxane, under agitation. Into the vortex of this blend is sifted a carbomer—Carbopol 940— a water soluble polymer of acrylic acid-crosslinked with a polyallyl sucrose, from B. F. Goodrich Company having a molecular weight of about 4 million, a specific gravity of 1.41, an equivalent weight of 76±4 and a Tg of 100°–105° C. The carbomer (gelling agent) is mixed until it is completely dispersed and wetted.

Glycerol (glycerine), DL-panthenol, fragrance, deionized water, and UCON 75H450 fluid—a polyethylene glycol (17 moles)/polypropylene glycol (6 moles) (17PEG/6PPG) copolymer from Union Carbide, molecular weight 1300, were added with continued mixing until the resulting blend was throughly dispersed and uniform. Finally, triethanolamine was added under continuous mixing until the resulting product became thick and uniform.

The resulting skin care product is applied to the skin as a conditioning refresher to freshen the skin, to condition it and to alleviate the symptoms of dry skin.

The skin care formulation thus prepared had the following composition:

| COMPOSITION A | |
|---|---|
| Ingredients | Weight Percent |
| Denatured Alcohol | 48.0 |
| Dimethicone | 1.0 |
| Cyclomethicone | 1.0 |
| Carbopol 940 | 0.3 |
| Glycerol | 3.0 |
| 17PEG/6PPG Copolymer | 2.0 |
| dl-Panthenol | 2.0 |
| Triethanolamine | 0.16 |
| Fragrance | 0.25 |
| Deionized Water | 42.29 |

The identical composition was prepared except that DL-panthenol was omitted. This composition was designated—Composition B. Composition A and Composition B were subjected to a tape stripping test in accordance with the procedure set forth hereinbefore. Composition A, after 210 minutes, exhibited no dry skin particles on the tape. The treated skin did not show flaking or scaling. Composition B, on the other hand, without DL-panthenol, showed flaking and scaling only 90 minutes after application.

EXAMPLE II

To further illustrate the beneficial properties, particularly softness, imparted to the skin by the present invention the following preparations 'C' and 'D' were formulated in accordance with the procedure of Example I with the exception that Cocoa Butter was melted and added to the mixtures after the Carbopol addition:

| Ingredients | Weight Percent | |
|---|---|---|
| | Composition C | Composition D |
| *Denatured Ethanol | 48.17 | 48.17 |
| **Dimethylpolysiloxane | 0.83 | 0.83 |
| Cocoa Butter | 1.0 | 1.0 |
| ***Acrylic Carbomer | 0.366 | 0.59 |
| Glycerine | 3.616 | 3.616 |
| ****17PEG/6PPG Polyether | 3.616 | 2.5 |
| dl-Panthenol | 3.616 | 0.76 |
| Triethanolamine | 0.18 | 0.3 |
| Fragrance | 0.35 | 0.35 |
| Deionized Water | 38.26 | 41.88 |

*SDA 40 Alcohol
**Dimethicone (Dow Corning 225 Fluid)
***Carbopol 940 (B. F. Goodrich)
****UCON 75H450 (Union Carbide)

To determine the effect of these skin refreshing formulations on skin softening, 0.1 ml of the product was rubbed over an area of 3 $cm^2$ for 40 seconds at a point 1 cm above the webs of the finger. The quasi-modulus of elasticity values of treated and untreated control skin were measured by the GBE method. The property being measured is the stiffness of the treated skin. Any decrease in the modulus as an indication of increased skin softening. The results are as follows:

| Composition | Untreated Control | 3 Minutes After Application | 20 Minutes After Application |
|---|---|---|---|
| C | 6.49 ± 1.84 | 5.38 ± 1.17 | 5.42 ± 1.38 |
| D | 6.41 ± 1.33 | 5.04 ± 1.06 | 5.28 ± 1.40 |

The results after three minutes are statistically significant and show a significant reduction from the untreated control (0.05).

A test series run with JEAN NATE splash did not show any softening effects after 3 or 20 minutes.

EXAMPLE III

In order to illustrate the unexpected effects imparted by the base composition of the invention compositions E and F were prepared. Composition F did not contain a panthenyl moisturizer. The ingredients were mixed together with stirring to provide the following base compositions:

| | Composition E Weight Percent | Composition F Weight Percent |
|---|---|---|
| Glycerine | 33⅓% | 33⅓% |
| 17PEG/6PPG Polyether | 33⅓% | 33⅓% |
| DL-panthenol | 33⅓% | — |
| Deionized Water | — | 33⅓% |

The compositions were tested in accordance with the sebumeter and tape stripping procedures set forth hereinbefore. The untreated skin exhibited a sebumeter baseline meter reading of 8. After application of the blends E and F the readings exceeded 50 for 90 minutes with blend F, and exceeded 50 for 180 minutes with blend E. Tape stripping showed corneocytes being removed from the area treated with blend F after 150 minutes and with blend E after 180 minutes. The results demonstrate the extended conditioning and protection against drying imparted by the base compositions of the invention.

EXAMPLE IV

A facial cream, composition H, was prepared substantially in accordance with the procedure of Example I. A comparative cream was prepared, composition G, without a novel base composition of the invention. The compositions were as follows:

| | Composition G Weight Percent | Composition H Weight Percent |
|---|---|---|
| Stearic Acid, Triple pressed | 20.0 | 20.0 |
| Lanolin | 1.0 | 1.0 |
| Polypropylene Glycol Ether of Stearyl Alcohol | 3.0 | 3.0 |
| Glycerol Monostearate | 3.0 | 3.0 |
| Propylene Glycol | 3.0 | 3.0 |
| Triethanolamine | 0.6 | 0.6 |
| Moisturizing Blend E Example III | — | 12.5 |
| Water | 69.4 | 56.9 |
| Preservative | q.s. | q.s. |

The compositions were tested as in Example III. Sebumeter values were 5.5 points higher for composition H with the moisturizing base composition of the invention than with composition G. Tape stripping of composition G produced a value of 30, while composition H with the inventive moisturizing blend had a value of 13. The value of 1 indicates no scale is removed. The lower the value the more moist the skin.

The results clearly demonstrate the superiority of the skin care creams of the invention employing the moisturizing base compositions of the invention.

EXAMPLE V

Hand and body lotions were prepared substantially in accordance with the procedures of Example I. Composition I did not contain the moisturizing blend of Example III and utilized an equivalent amount of water. The compositions were as follows:

| | Composition I Weight Percent | Composition J Weight Percent |
|---|---|---|
| Mineral Oil | 20.0 | 20.0 |
| Cetyl Alcohol | 5.0 | 5.0 |
| Arlacel 60 (Sorbitan Stearate) | 2.5 | 2.5 |
| Tween 60 (Polysorbate 60) | 7.5 | 7.5 |
| Moisturizing Blend E Example III | — | 12.5 |
| Water | 65.0 | 52.5 |

|  | Composition I Weight Percent | Composition J Weight Percent |
|---|---|---|
| Preservative | q.s. | q.s. |

Sebumeter and tape stripping tests were conducted. The Sebumeter value for composition I was 143 and for composition J, with the moisturizing blend of Example III, was 178 after equivalent periods. After 45 minutes the sebumeter values of composition J were twice those of composition I. Tape stripping of composition I resulted in a value of 22, while composition J exhibited a value of 7.

EXAMPLE VI

Two after-shave lotions were prepared substantially in accordance with the preparation procedures described hereinbefore. Composition L contained the moisturizing blend of Example III, while Composition K employed an equivalent amount of water. The compositions were as follows:

|  | Composition K Weight Percent | Composition L Weight Percent |
|---|---|---|
| Emerest 2314 (Isopropyl Myristate) | 2.0 | 2.0 |
| Propylene Glycol | 0.5 | 0.5 |
| Deionized Water | 17.5 | 5.0 |
| Moisturizing Blend E Example III | — | 12.5 |
| Ethyl Alcohol (SDA 40) | 80.0 | 80.0 |

The Sebumeter values for compositions K showed no improvement from normal baseline, while composition L had a value of 61.5. Tape stripping values for composition K totaled 30, while the values for composition L with the moisturizing blend, totaled 13.

EXAMPLE VII

Two shave creams were prepared substantially in accordance with the procedure of Example I. Compositions M and N were prepared and thereafter 95% soap solutions designated M' and N', were formulated into an aerosol with isobutane and propane as propellants. Composition N contained moisturizing blend E of Example III, while composition M contained an equivalent amount of water. The compositions were as follows:

|  | Composition M Weight Percent | Composition N Weight Percent |
|---|---|---|
| Triethanolamine Stearate | 8.0 | 8.0 |
| Triethanolamine soap of coconut fatty acids | 2.0 | 2.0 |
| Water | 90.0 | 78.5 |
| Moisturizing Blend E Example III | — | 12.5 |

|  | Composition M' | Composition N' |
|---|---|---|
| Soap solution (as above) | 95 (Composition M) | 95 (Composition N) |
| Isobutane | 4.28 | 4.28 |
| Propane | 0.72 | 0.72 |

The products M' and N' were applied to wet skin, spread around and allowed to remain for one minute to simulate shave conditions. Thereafter, they were lightly scraped from skin using a blunt object, such as a spatula blade. The sebumeter shows an increase of product M' values over product N' values. The tape stripping value for M' was 30 while the tape stripping value for N' was 18.

EXAMPLE VIII

Sunscreen lotions O and P were prepared having the same ingredients as compositions I and J of Example V with the addition of a sunscreen, Escalol 507, octyl dimethyl paraaminobenzoate. The compositions were as follows:

|  | Composition O | Composition P |
|---|---|---|
|  | 95 (Composition I) | 95 (Composition J) |
| Escalol 507 | 5 | 5 |

The compositions were tested with the following results. Sebumeter values were in excess of 200 for composition P and were 179 for composition O. Tape stripping value for composition O was 16 and for composition P was 9.

EXAMPLE IX

Two shampoo compositions Q and R were prepared by mixing AGREE SHAMPOO, from S. C. Johnson & Son, Inc. and moisturizing blend E of Example III for composition R and by utilizing AGREE SHAMPOO, alone, for composition Q. The compositions were tested with the following results:

|  | Composition Q Weight Percent | Composition R Weight Percent |
|---|---|---|
| AGREE Shampoo | 100 | 87.5 |
| Moisturizing Blend E | — | 12.5 |

Hair swatches were washed using compositions Q and R. Composition R exhibited less fly-away and more shine than composition Q without the moisturizing blend.

EXAMPLE X

Two cream rinses were evaluated by employing AGREE CREME RINSE, from S. C. Johnson & Son, Inc. as composition S and by adding moisturizing blend E of Example III to the AGREE CREME RINSE as composition T. The compositions were tested as follows:

|  | Composition S Weight Percent | Composition T Weight Percent |
|---|---|---|
| Agree Creme Rinse | 100 | 87.5 |
| Moisturizing Blend E Example III | — | 12.5 |

Two hair swatches were washed with shampoo and rinsed separately with compositions S and T. The swatch rinsed with composition T showed less flyaway and more shine.

EXAMPLE XI

Two hydroalcoholic gels were prepared substantially in accordance with the procedure of Example I; composition V utilizing moisturizing blend E of Example III, while composition U employed an equivalent amount of water. The compositions were prepared and tested as follows:

|  | Composition U Weight Percent | Composition V Weight Percent |
|---|---|---|
| Ethanol (100%) - SDA 40 Alcohol | 50 | 50 |
| Dimethyl polysiloxane - Carbopol 940 | 0.3 | 0.3 |
| Triethanolamine | 0.16 | 0.16 |
| Moisturizing Blend E Example III | — | 12.5 |
| Water | 49.54 | 37.04 |

The Sebumeter value for composition U was −1.5, while the reading for composition V with the moisturizing blend was 38.5. The tape stripping value for composition U was 30 and for composition V was 7.

EXAMPLE XII

The hydroalcoholic gels of Example XI were formulated into sunscreen gels, W and X by the addition of 5% by weight of Escalol 507, octyl dimethyl paraaminobenzoate. Composition W contained moisturing blend E of Example III. The compositions were tested as follows:

The Sebumeter value for composition X was 54.5 and for composition W with the moisturizing blend, the value was 124. The tape stripping value for composition X was 30 and for composition W was 16.

EXAMPLE XIII

Two aerosol pump sprays Y and Z were prepared and tested as follows:

|  | Composition Y Weight Percent | Composition Z Weight Percent |
|---|---|---|
| Ethanol (95%) - SDA 40 Alcohol | 25 | 25 |
| Dimethicone (Dow Corning 225 Fluid) | 5 | 5 |
| Moisturizing Blend E Example III | — | 15 |
| Deionized Water | 70 | 70 |

The Sebumeter value for composition Y was 8, while for composition Z with the moisturizing blend, it was 130. The tape stripping value for composition Y was 21 and for composition Z was 10.

EXAMPLE XIV

Two astringent after shave and toner splashes, A-1 and A-2 were prepared as follows:

|  | Composition A-1 Weight Percent | Composition A-2 Weight Percent |
|---|---|---|
| Witch Hazel Extract | 15.0 | 15.0 |
| Alcohol | 10.0 | 10.0 |
| Alum | 0.5 | 0.5 |
| Menthol | 0.05 | 0.05 |
| Ethyl p-Aminobenzoate | 0.05 | 0.05 |
| Glycerine | 5.0 | — |
| Moisturizing Blend E Example III | — | 12.5 |
| Water | 69.4 | 61.9 |

The splashes were tested with the result that the Sebumeter value for composition A-1 was 3, while for composition A-2 with the moisturizing blend, it was 95.5. The tape stripping value for composition A-1 was 30 and for composition A-2, it was 7.

EXAMPLE XV

Two sunscreen creams were prepared by adding 5% by weight Escalol 507, octyl dimethyl paraaminobenzoate, to compositions G and H of Example IV to yield compositions G-1 and H-1. The compositions were tested and the Sebumeter value for composition G-1 was 2.5, while for composition H-1 with moisturizing blend E of Example III, it was 21. The tape stripping results for composition G-1 was 29 and for composition H-1 was 21.

EXAMPLE XVI

Two soft soap products were prepared; one product, B-2, contained 12.5% of moisturing blend E of Example III, while the other, B-1, was 100% soft soap. The products were tested and both products foamed comparably during normal hand washing. B-2 left a smoother, softer feeling to the hands after drying.

EXAMPLE XVII

Two stick deodorant-antiperspirant products, C-1 and C-2 were prepared as follows:

|  | Composition C-1 Weight Percent | Composition C-2 Weight Percent |
|---|---|---|
| Polyethylene Glycol (MW 20,000) | 3.0 | 3.0 |
| Sodium Stearate | 3.0 | 3.0 |
| Sodium Chloride | 2.0 | 2.0 |
| Preservative | 0.1 | 0.1 |
| Fragrance | 0.5 | 0.5 |
| Moisturizing Blend E Example III | — | 12.5 |
| Deionized Water | 91.4 | 78.9 |

The products were tested and C-1 showed a sebumeter value of 2 while C-2 with the moisturizing blend, had a value of 49. The tape stripping value for C-1 was 30 and for C-2 was 6.

EXAMPLE XVIII

Two insect repellent lotions R-1 and R-2 were prepared as follows:

|  | Composition R-1 Weight Percent | Composition R-2 Weight Percent |
|---|---|---|
| Carbopol 934 | 0.31 | 0.27 |
| Perfume | 0.50 | 0.44 |
| Steareth-2 (Brij 72) | 0.75 | 0.66 |
| Stearyl Alcohol | 1.00 | 0.87 |
| Glyceryl Stearate & PEG 100 Stearate (Arlacel 165) | 1.00 | 0.87 |
| N,N-diethyl-m-toluamide | 30.00 | 26.25 |
| 2,3,4,5-bis-(2-butylene)-tetrahydro-2-furfural | 1.0 | 0.87 |
| Octylbicycloheptene dicarboximide | 4.0 | 3.5 |
| Triethanolamine | 0.80 | 0.71 |
| Metyl Paraben | 0.10 | 0.09 |
| Moisturizing Blend E Example III | — | 12.50 |
| Deionized Water | 60.54 | 52.97 |

The products were tested and R-1 had a sebumeter value of in excess of 50 for 30 minutes and R-2 had a sebumeter value of in excess of 50 for 60 minutes. The tape stripping value for R-1 was 27 and R-2 was 18.

While various preferred embodiments of the present invention have been illustrated by means of specific examples, it is to be understood that the present invention is in no way to be deemed limited thereto.

Wherefore we claim:

1. A non-oily, non-occlusive water soluble base composition for personal care compositions providing enhanced skin or hair conditioning and extended protection against drying comprising:
   (a) a panthenol moisturizer selected from the group consisting of dexpanthenol, DL-panthenol, and mixtures thereof, and
   (b) an emollient comprising:
      (i) a polyhydric alcohol humectant selected from the group consisting of propylene glycol, glycerol, and mixtures thereof, and
      (ii) a polyether derivative selected from the group consisting of copolymers of polyethylene glycol and polypropylene glycol, and mixtures thereof,
   wherein the weight ratio of emollient (b) to the moisturizer (a) is from about 33:1 to 0.54:1, the weight ratio of humectant (i) to moisturizer (a) is from about 15:1 to 0.28:1, the weight ratio of polyether derivative (ii) to moisturizer (a) is from about 15:1 to 0.28:1 and the weight ratio of the moisturizer (a) to the emollient (b) is sufficient to provide effective conditioning and to maintain cutaneous moisture and oil levels.

2. The composition of claim 1 wherein the polyhydric alcoholic humectant is glycerol.

3. The composition of claim 1 wherein the weight ratio of emollient (b) to moisturizer (a) is from about 18:1 to 3:1.

4. The composition of claim 1 wherein the weight ratio of humectant (i) to moisturizer (a) is from about 10:1 to 3.2:1 and the weight ratio of polyether derivative (ii) to moisturizer (a) is from about 10:1 to 1.2:1.

5. The composition of claim 4 wherein the polyether derivative has a molecular weight of from about 1,000 to 2,000 daltons.

6. The composition of claim 5 wherein the polyether derivative has a molecular weight of about 1,300 daltons and is formed from copolymerizing 17 moles of polyethylene glycol per 6 moles of polypropylene glycol.

7. The composition of claim 1 wherein the polyether derivative has a molecular weight of about 1,300 daltons and is formed from copolymerizing 17 moles of polyethylene glycol per 6 moles of polypropylene glycol and the weight ratio of emollient (b) to moisturizer (a) is from about 18:1 to 3:1.

8. The composition of claim 7 wherein the weight ratio of humectant (i) to moisturizer (a) is from about 10:1 to 3.2:1 and the weight ratio of polyether derivative (ii) to moisturizer (a) is from about 10:1 to 1.2:1.

9. The composition of claim 1 wherein the polyhydric humectant is glycerol and the weight ratio of emollient (b) to moisturizer (a) is from about 18:1 to 3:1.

10. The composition of claim 9 wherein the polyether derivative is a copolymer of polyethylene glycol and polypropylene glycol having a molecular weight of from about 1,000 to 2,000 daltons.

11. The composition of claim 10 wherein the weight ratio of humectant (i) to moisturizer (a) is from about 10:1 to 3.2:1 and the weight ratio of polyether derivative (ii) to moisturizer (a) is from about 10:1 to 1.2:1.

12. An aqueous skin conditioning composition consisting essentially of from about 1 to 15% by weight of the total weight of the composition of a base comprising (a) up to 5% by weight of the total composition of a panthenol moisturizer selected from the group consisting of dexpanthenol, DL-panthenol, and mixtures thereof, and (b) an emollient comprising: (i) up to about 5% by weight of the total composition of a polyhydric alcohol humectant selected from the group consisting of propylene glycol, glycerol, and mixtures thereof, and (ii) up to about 5% by weight of the total composition of a polyether derivative selected from the group consisting of copolymers of polyethylene glycol and polypropylene glycol, and mixtures thereof, from about 1 to 3% by weight of silicone fluid, up to about 50% by weight of a gelling agent, optionally from 1 to 10% by weight of an emulsifier selected from the class of nonionic, anionic, amphoteric and cationic emulsifiers, and deionized water, wherein the amount of water, gelling agent and any emulsifier present is such to provide a composition which can be uniformly spread on the skin, and the weight ratio of emollient (b) to the moisturizer (a) is from about 33:1 to 0.54:1, the weight ratio of humectant (i) to moisturizer (a) is from about 15:1 to 0.28:1, the weight ratio of polyether derivative (ii) to moisturizer (a) is from about 15:1 to 0.28:1 and the weight ratio of the moisturizer (a) to the emollient (b) is sufficient to provide effective conditioning and to maintain cutaneous moisture and oil levels.

13. The composition as claimed in claim 12 wherein the amount of moisturizer (a) is from about 0.3 to 3.6% by weight, humectant (i) is from about 1 to 4.2% and polyether derivative (ii) is from about 1 to 4.2% by weight.

14. The composition as claimed in claim 12 wherein the gelling agent is a neutralized gelling agent wherein the neutralizing agent is selected from the group consisting of triethanolamine, triethylamine, isopropylamine, potassium hydroxide and sodium hydroxide and the gelling agent is a polyacrylic acid crosslinked with a polyether of an oligosaccharide.

15. The composition as claimed in claim 12 wherein humectant (i) is glycerol and polyether derivative (ii) has a molecular weight of from about 1,000 to 2,000 daltons.

16. The composition as claimed in claim 15 wherein the weight ratio of emollient (b) to moisturizer (a) is from about 18:1 to 3:1.

17. The composition as claimed in claim 15 wherein the weight ratio of humectant (i) to moisturizer (a) is from about 10:1 to 3.2:1 and the weight ratio of polyether derivative (ii) to moisturizer (a) is from about 10:1 to 1.2:1.

18. The composition of claim 17 wherein the polyether derivative has a molecular weight of about 1,300 daltons and is formed from copolymerizing 17 moles of polyethylene glycol per 6 moles of polypropylene glycol.

19. The composition as claimed in claim 15 wherein the gelling agent is a neutralized gelling agent wherein the neutralizing agent is selected from the group consisting of triethanolamine, triethylamine, isopropylamine, potassium hydroxide and sodium hydroxide and the gelling agent is a polyacrylic acid crosslinked with a polyether of an oligosaccharide.

20. The composition as claimed in claim 15 wherein the amount of moisturizer (a) is from about 0.3 to 3.6% by weight, humectant (i) is from about 1 to 4.2% and polyether derivative (ii) is from about 1 to 4.2% by weight.

* * * * *